United States Patent [19]
Yano et al.

[11] Patent Number: 5,858,975
[45] Date of Patent: Jan. 12, 1999

[54] OXYNTOMODULIN PEPTIDE HAVING CARDIOTONIC ACTIVITY AND INSULIN RELEASE-BROMATING ACTIVITY

[75] Inventors: Keiichi Yano, Kawasaki; Motoo Yamasaki, Machida; Takahiro Moriyama, Ichikawa; Masaaki Ando, Higashihiroshma, all of Japan

[73] Assignee: Kyowa Hakko Kogyo Co., Ltd., Tokyo, Japan

[21] Appl. No.: 836,528

[22] PCT Filed: Nov. 7, 1995

[86] PCT No.: PCT/JP95/02269

§ 371 Date: May 2, 1997

§ 102(e) Date: May 2, 1997

[87] PCT Pub. No.: WO96/14336

PCT Pub. Date: May 17, 1996

[30] Foreign Application Priority Data

Nov. 7, 1994 [JP] Japan .................................. 6-272069

[51] Int. Cl.$^6$ .............................. A61K 38/23; C07K 5/04
[52] U.S. Cl. .............................. 514/12; 514/21; 514/866; 530/308; 530/324
[58] Field of Search ................................ 514/12, 21, 866; 530/308, 321; 930/10

[56] References Cited

PUBLICATIONS

Conlon et al., Gen. & Comp. Endocrinology, vol. 72 (1988) 181–189.
Bataille et al., FEBS Letters, vol. 146, No. 1 (Sep. 1982) 73–78.
Conlon et al., Regulatory Peptides, vol. 11 (1985) 309–320.
Kervran et al., Endocrinology, vol. 121, No. 1 (1987) 704–713.
Conlon et al., Biochem. J., vol. 245 (1987) 851–855.
Shinomura et al., Regulatory Peptides, vol. 23 (1988) 299–308.
Pollock et al., Journal of Biol. Chem., vol. 263, No. 20 (1988) 9746–51.
Pollock et al., Gen. & Comp. Endocrinology, vol. 69 (1988) 133–140.
Tanbi et al., Biochimica et Biophysica Acta, vol. 1095 (1991) 249–254.
Biedzinski et al., Peptides, vol. 8 (1987) 967–972.
Jarrousse et al., Endocrinology, vol. 115, No. 1, (1984) 102–105.
Depigny et al., C.R. Acad. Sc., Paris, vol. III, No. 16 (1984) 677–680.
Otani et al., J. Biochem., vol. 79, No. 2 (1976) 345–352.
Azria et al., Progress in Clin. Biochem. & Med., vol. 9, Calcitonins, 1–34 (1989).
Bataille et al., FEBS Letters, vol. 146, No. 1 (1982) 79–87.
Gros et al., Eur. Journal. Pharm., Mol. Pharm. Sec. 288 (1995) 319–327.
Gros et al., Endocrinology, vol. 130, No. 3 (1992) 1263–1270.
Collie et al., Proc. Natl. Acad. Sci., vol. 91 (Sep. 1994) 9362–9366.
Nathan et al., Diabetes Care, vol. 15, No. 2 (Feb. 1992) 270–276.

*Primary Examiner*—Christina Y. Chan
*Assistant Examiner*—Mary Beth Tung
*Attorney, Agent, or Firm*—Fitzpatrick, Cella, Harper & Scinto

[57] ABSTRACT

An oxyntomodulin peptide has cardiotonic activity and insulin release-promoting activity. The peptide or pharmaceutical salts thereof can be used for prevention or treatment of cardiopathy or diabetes.

3 Claims, 3 Drawing Sheets

OXYNTOMODULIN PEPTIDE HAVING CARDIOTONIC ACTIVITY AND INSULIN RELEASE-BROMATING ACTIVITY

This application is a 371 of PCT/JP95/02269, filed Nov. 7, 1995.

BACKGROUND OF THE INVENTION

1. Field of the Invention

The present invention relates to a novel peptide or Pharmaceutically acceptable salts thereof, which have cardiotonic activity and insulin release-promoting activity and are useful for prevention or treatment of cardiopathy or diabetes.

BRIEF DESCRIPTION OF THE BACKGROUND ART

Oxyntomodulin (hereinafter referred to as OXM) is a peptide which is produced by post-translational processing of proglucagon, like glucagon (peptide composed of 29 amino acids), glucagon-like peptides and glicentin, and is recognized to exist in intestines and hypothalamus. OXM has a structure of glucagon or glucagon-like peptide to which are added 7 or 8 amino acid residues at its carboxyl terminal, and its structures in porcine (D. Bataille et al., FEBS Lett., 146, 73–78, 1982), in bovine (J. M. Conlon et al., Regul. Pept., 11, 309–320, 1985), in rat (A. Kervran et al., Endocrinol., 121, 704–713, 1987), in shark (J. M. Conlon et al., Biochem. J., 245, 851–855, 1987), in canine (Y. Shinomura et al., Regul. Pept., 23, 299–308, 1988), in bullfrog (H. G. Pollock et al., J. Biol. Chem., 263, 9746–9751, 1988), and in alligator (H. G. Pollock et al., Gen. Comp. Endocrinol., 69, 133–140, 1988) have been clarified at present. The primary structures of OXM of every species are similar to each other, having neither cysteine residue nor proline residue in the molecule. Regarding the physiological activities of OXM, for example, its somatostatin secretion-promoting activity (T. Tani et al., Biochim. Biophys. Acta, 1095, 249–254, 1991), its gastric acid secretion-inhibiting activity (T. M. Biedzinski et al., Peptides, 8, 967–972, 1987), and its insulin secretion-promoting activity (C. Jarrousse et al., Endocrinol., 115, 102–105, 1984) have heretofore been reported. It is believed that OXM may exhibit its physiological functions via a receptor which is different from that for glucagon (C. Depigny et al., C.R. Acad. Sci. III (France), 299, 677–680, 1984). However, this belief has not been completely clarified as yet. Though being similar to glucagon in its primary structure, OXM obviously differs from glucagon, for example, in its distribution in tissue and its gastric acid secretion-inhibiting activity. To further clarify the physiological activities of OXM, the analysis of its structures in further lower animals is also important. For example, regarding the effect of calcitonin on calcium concentration on the rat plasma, it is known that the effect of eel calcitonin is obviously higher than those of rat, porcine and human calcitonins (M. Otani et al., J. Biochem., 79, 345–352, 1976; M. Azria, Prog. Clin. Biochem. Med., 9, 1–33, 1989). However, the presence of eel OXM, the structure thereof and the physiological activities thereof are not known up to these days.

SUMMARY OF THE INVENTION

We, the present inventors have variously studied substances existing in eel intestines, and as a result, have found a novel factor having atrial contractile activity. As a result of having further studied it, we have found that this factor is a novel peptide, while having a cardiotonic activity and an insulin release-promoting activity, and is therefore useful as a medicine for cardiopathy, diabetes, etc. On the basis of these findings, we have completed the present invention.

DETAILED DESCRIPTION OF THE INVENTION

Specifically, the present invention relates to a peptide of the following formula (I):

H-His-Ser-Gln-Gly-Thr-Phe-Thr-Asn-Asp-Tyr-Ser-Lys-Tyr-Leu-Glu-Thr-Arg-Arg-Ala-Gln-Asp-Phe-Val-Gln-Trp-Leu-Met-Asn-Ser-Lys-Arg-Ser-Gly-Gly-Pro-Thr-OH (SEQ ID NO:1)(I) or pharmaceutically acceptable salts thereof.

The abbreviations for the corresponding amino acids in formula (I) are generally used in this technical field, which are as follows:

Ala: L-alanine
Arg: L-arginine
Asn: L-asparagine
Asp: L-aspartic acid
Gln: L-glutamine
Glu: L-glutamic acid
Gly: Glycine
His: L-histidine
Leu: L-leucine
Lys: L-lysine
Met: L-methionine
Phe: L-phenylalanine
Pro: L-proline
Ser: L-serine
Thr: L-threonine
Trp: L-tryptophan
Tyr: L-tyrosine
Val: L-valine The pharmaceutically acceptable salts of the peptide of formula (I) include salts with inorganic acids such as hydrochlorides, sulfates and phosphates; and salts with organic acid such as acetates, maleates, fumarates, tartrates, citrates, lactates and methanesulfonates.

The peptide of the present invention is a novel OXM, the structure of which is different from those of any other known OXMs. Specifically, in known OXMs, the 15th amino acid residue from the amino terminal is Asp and the 35th residue therefrom is Asn or Ile, while the peptide of the present invention is characterized in that the 15th residue thereof is Glu and the 35th residue thereof is Pro.

The peptide of the present invention can be obtained according to a method of collecting it from cells that produce the said peptide, or according to organic synthetic means. The cells that produce the said peptide may include the eel intestinal tissue cells, the cells as grown by cultivating them, the cells as transformed according to genetic recombination to produce the intended peptide, etc.

To extract and isolate the peptide of the present invention from eel intestines, eel intestines are homogenized in suitable acidic solution, for example, in an aqueous solution of acetic acid, hydrochloric acid or the like, insoluble substances are removed from the resulting homogenate through centrifugation to obtain a liquid extract, and thereafter this liquid extract is subjected to a combination of any treatments generally employed for isolation and purification of peptides such as fractional precipitation with an organic solvent, solvent extraction, dialysis, ultrafiltration, ion-exchange chromatography, adsorption chromatography, gel permeation chromatography, high-performance liquid chromatography, crystallization and electrophoresis, thereby obtaining the substance having the corresponding molecular weight.

To obtain the peptide of the present invention according to genetic recombination, DNA parts each coding for the N-terminal side and the C-terminal side of the said peptide are separately synthesized, then cloned separately, linked together optionally via an oligonucleotide linker, and introduced into a suitable expression vector according to an ordinary means, and then a host such as *Escherichia coli*, yeast and animal cells is transformed with the obtained vector, and the resulting transformant is incubated. As the means of expressing genes, there have heretofore been developed direct methods, secretion methods and fusion methods. Any of these methods may be employed in the present invention. For example, referred to are the methods described in J. Sambrook et al., "Molecular Cloning 2nd Edition", Cold Spring Harbor Lab. Press, N.Y. (1989). To isolate and purify the peptide of the present invention from these cells, employable is any combination of the above-mentioned ordinary means for the isolation and purification of peptides.

It is also possible to chemically synthesize the peptide of the present invention from amino acids on the basis of the amino acid information of the said peptide. For such synthesis, employable are any ordinary peptide synthesizing methods, such as liquid phase methods and solid phase methods. For example, referred to are the methods described in H. Yajima & S. Yanagihara, Seikagaku Jikken Kouza (I): Tanpakushitu no Kagaku, Vol. 4 (edited by the Japanese Biochemical Society, published by Tokyo Kagaku Dojin, 1977); and N. Izumiya et al., "Pepuchido Gousei no Kiso to Jikken" (published by Maruzen, 1985).

Where solid phase methods are employed for obtaining the peptide, p-benzyloxybenzyl alcohol-type resins (e.g., polystyrene) are preferred as the support. For these, for example, commercial products comprising a resin of that type, to which is bonded an α-amino-protected amino acid via ester bonding, are available. For these, preferably, the α-amino groups of the amino acid to be used are protected with 9-fluorenylmethoxycarbonyl (Fmoc) groups; the guanidino groups of arginine is with 2,2,5,7-pentamethylchroman-6-sulfonyl (Pmc) groups; the β- and γ-carboxylic acids of aspartic acid and glutamic acid, and the hydroxyl groups of serine, threonine and tyrosine are with t-butyl (tBu) groups; the β- and γ-amido groups of asparagine and glutamine, and the imidazolel groups of histidine are with trityl (Trt) groups; and the ε-amino groups of lysine is with t-butyloxycarbonyl (Boc) groups. The condensation of the protected amino acids is preferably conducted, using a condensing agent, such as dicyclohexylcarbodiimide (DCC) and benzotriazol-1-yl-oxytripyrrolidinophosphonium hexafluorophosphate (PyBOP) in the presence of N-hydroxybenzotriazole (HOBt). As the solvent preferably used is N,N-dimethylformamide (DMF), and the deprotection of Fmoc groups is preferably effected with N-methylmorpholine (NMM) The amino acids are prolonged in order to give a protected peptide resin, which is processed with an acid such as trifluoroacetic acid (TFA) in the presence of a sulfur-containing compound such as thioanisole, ethanediol, ethylmethylsulfide and thiophenol, to give a crude synthetic peptide. In ordinary condensation, the protected amino acid, the condensing agent and HOBt are used each in an amount of from 1 to 15 equivalents relative to the hydroxyl groups of the resin or to the amino acids as bonded first to the resin. Such ordinary condensation is effected at room temperature for from 30 minutes to 5 hours. To release the synthetic peptide from the resin, the resin may be processed at room temperature for from 1 to 10 hours. To purify the thus-obtained peptide, employable is any combination of the above-mentioned ordinary means for isolation and purification of peptides.

Now, the pharmaceutical effects of the peptide (eel OXM) of formula (I) are mentioned in the following Test Examples.

Test Example 1 Effect of OXM in Eel Atrium

Figure 1:
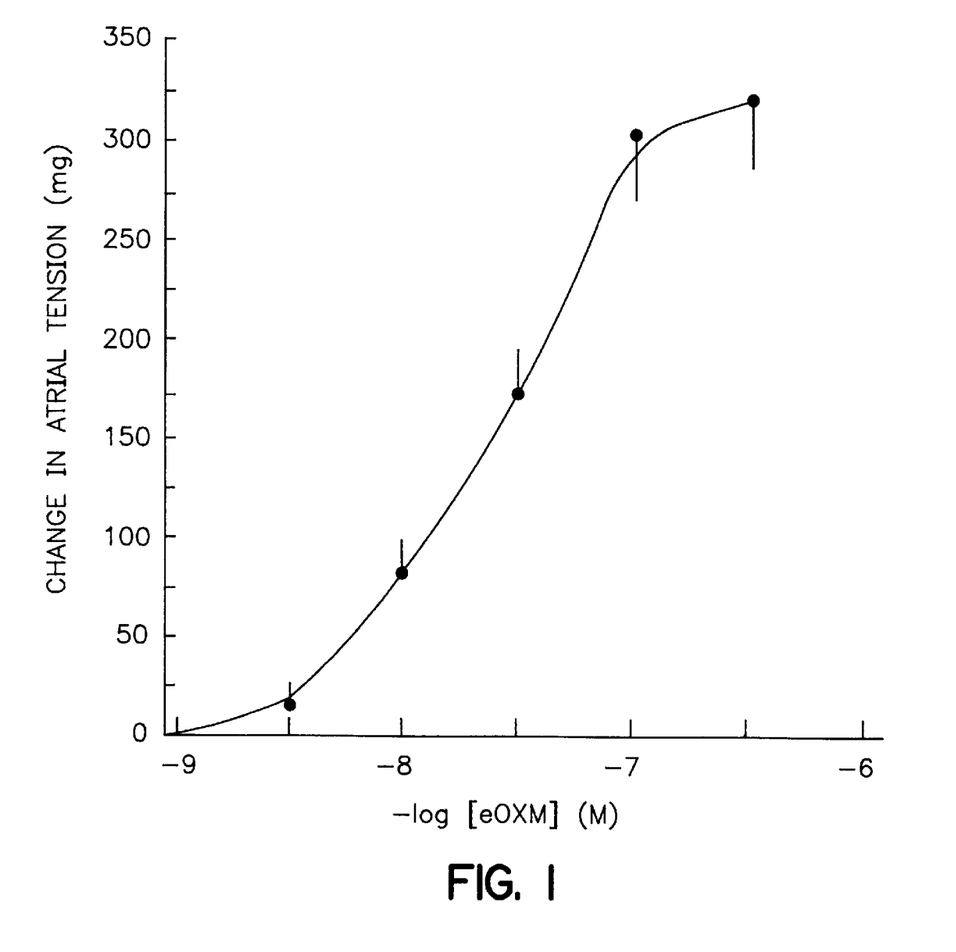
FIG. 1 shows the effect of Oxyntomodulin on eel atrial systole.
Figure 2:
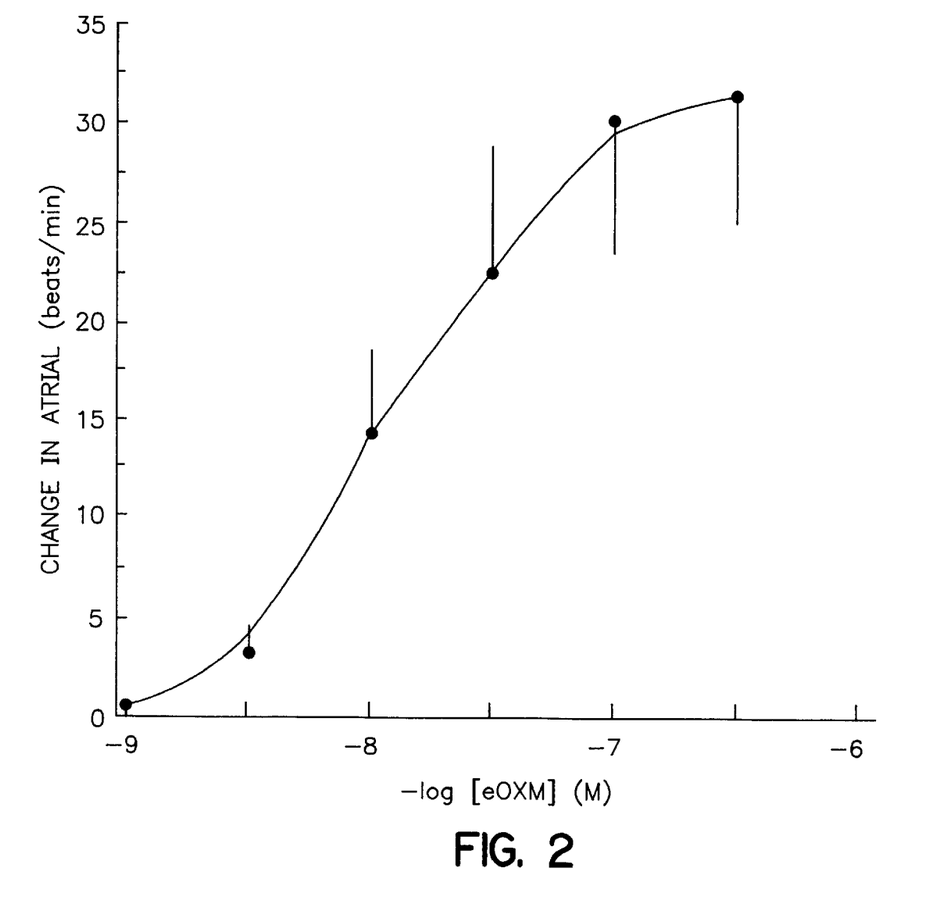
FIG. 2 shows the effect of Oxyntomodulin on eel atrial rate.

An atrium was taken out of an eel, and one end of said atrium was fixed to the bottom of syringe filled with 1.5 ml of Ringer's solution in which was introduced a mixed gas of oxygen and carbon dioxide (95:5), while the other end thereof was connected to a tension transducer (NEC) via a silk thread. 15 µl of an aqueous solution of OXM as diluted with distilled water to have a varying concentration was added to said Ringer's solution, whereupon the tension to be generated by the atrial contraction was measured through the tension transducer. OXM used herein was the product as produced in Example 2. During this measurement, the atrial rate was also counted. FIG. 1 shows the relationship between the concentration of OXM added and the atrial tension measured, and FIG. 2 shows the relationship between the OXM concentration and the atrial rate counted.

These data verify that OXM dose-dependently increases the atrial systole and the atrial rate.

Figure 3:
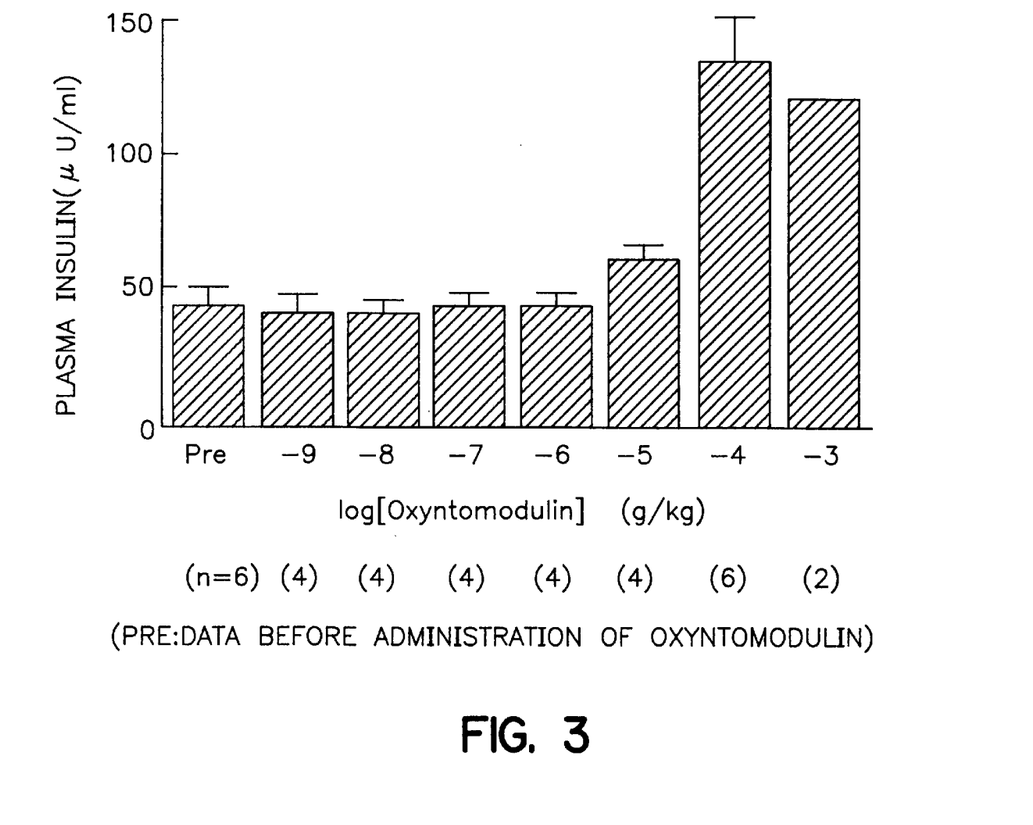
FIG. 3 shows the effect of Oxyntomodulin on rat plasma insulin concentration.

Test Example 2 Effect of OXM on Plasma Insulin Concentration of Anesthetized Rat Male SD rats (370 to 450 g) were bred with no feed for from 15 to 20 hours, and then Na pentobarbital (50 mg/kg) was intra-abdominally administered thereto. A blood-collecting cannula was inserted into the carotid artery of each rat. A dosed cannula was inserted into the jugular vein of each rat. About 600 µl of blood was collected from each rat before the administration of a test chemical, and 5 minutes after each administration of a varying dose of the said test chemical. OXM obtained in Example 2 was added to physiological saline solution to adjust concentration of 1 mg/ml. The said OXM solution was diluted with a physiological saline solution, the thus-diluted solution was accumulatively administered to each rat. The dose of the solution was 1 ml/kg. The collected blood was centrifuged, and its insulin concentration was measured according to the Insulin-EIA Test (Wako Pure Chemicals). The data obtained are shown in FIG. 3.

The data verify that OXM increases the plasma insulin concentration at a dose of 0.01 mg/kg or more.

The peptide of formula (I) and pharmaceutically acceptable salts thereof can be administered through various administration routes such as injection, intra-mucosal administration and peroral administration, and can be used with various dosage forms according to the said administration routes. The said dosage forms are, for example, intravenous injection, intramuscular injection, subcutaneous injection and intracutaneous injection; preparations for such injection to be dissolved before use, such as suspensions and lyophilized powders; preparations for intra-mucosal application, such as suppositories and per-nasal preparations; or peroral preparations, such as tablets, capsules, granules and suspensions. To prepare these dose forms, employable are any known methods. If desired, these preparations may be formulated to any additives that are acceptable for medicines, such as preservatives, stabilizers, antioxidants, vehicles, binders, disintegrators, wetting agents, lubricants, colorants, aromatics, flavors, filming agents, suspending agents, emulsifiers, dissolution aids, buffers, isotonicators, plasticizers, surfactants and analgesics.

Example of the carriers which can be used are water, distilled water for injection, physiological saline solution, glucose, fructose, sucrose, mannitol, lactose, starch, cellulose, methyl cellulose, carboxymethyl cellulose, hydroxypropyl cellulose, glycerin, xylitol, sorbitol, glucuronic acid, hyaluronic acid, heparin, chitin, chitosan, glycine, alanine, proline, serine, cysteine, aspartic acid, glutamic acid, lysine, arginine, human serum albumin, human serum globulin, collagen, gelatin, alginic acid, talc, sodium citrate, calcium carbonate, calcium hydrogenphosphate, magnesium stearate, urea, silicone resins, sorbitan fatty acid esters, glycerin fatty acid esters, ascorbic acid, α-tocopherol and the like.

The dose will vary, depending on the mode of administration, the age, the body weight and the symptoms of a patient, etc. However, it is generally appropriate to administer Compound(I) or a pharmaceutically acceptable salts thereof in a dose of 0.01 µg to 10 mg/60 kg/day.

Example 1 Isolation and Purification of Eel OXM 361 g of intestines as taken out of 150 eels were frozen with liquid nitrogen, ground, boiled in distilled water, homogenized in a mixture of 1M acetic acid and 20 mM hydrochloric acid, and centrifuged to collect the resulting supernatant liquid. Acetone was added to a final concentration of 66%, and the mixture was again centrifuged to remove the precipitate. The resulting supernatant liquid was passed through SEP-PAK PLUS® C18 (Waters), whereupon the substance as held therein was eluted with 50% acetonitrile, 10% isopropyl alcohol and 0.1% TFA (pH 2.2). The resulting eluate was purified through gel permeation chromatography using TOYOPEARL® HW-40F (2.6×100 cm) to which was applied an eluent comprised of 1M acetic acid and 10% isopropyl alcohol at a flow rate of 1.5 ml/min. Among the resulting fractions, those that exhibited the eel atrial contractile activity as referred to in Test Example 1 were purified through 5-stage high-performance liquid chromatography mentioned below.

First Stage:
  Column: ASAHIPAK® C8P-50 (4.6×250 mm, Asahi Chemical)
  Eluent: Solution A (10% isopropyl alcohol, 0.1% TFA)
    Solution B (50% acetonitrile, 10% isopropyl alcohol, 0.1% TFA)
  Mode: Linear gradient elution from solution A to solution B (for 50 minutes)
Second Stage:
  Column: TSKgel® ODS-80TM (4.6×250 mm, Toso)
  Eluent: Solution A (15% acetonitrile, 5% isopropyl alcohol, 0.1% TFA)
    Solution B (35% acetonitrile, 5% isopropyl alcohol, 0.1% TFA)
  Mode: Linear gradient elution from solution A to solution B (for 100 minutes)
Third Stage:
  Column: TSKGEL® CM-5PW (7.5×75 mm, Toso)
  Eluent: Solution A (20 mM phosphate buffer, pH 6.8, 10% isopropyl alcohol)
    Solution B (20 mM phosphate buffer, pH 6.8, 10% isopropyl alcohol, 350 mM sodium chloride)
  Mode: Linear gradient elution from solution A to solution B (for 35 minutes)
  Sodium chloride concentration at which OXM was eluted: 0.14M
Fourth Stage:
  Column: TSKGEL® ODS-80TM (4.6×150 mm, Toso)
  Eluent: Solution A (24% acetonitrile, 5% isopropyl alcohol, 0.1% TFA))
    Solution B (34% acetonitrile, 5% isopropyl alcohol, 0.1% TFA)
  Mode: Linear gradient elution from solution A to solution B (for 50 minutes)
  Retention Time of OXM: 31.5 minutes (organic solvent concentration: 33%)
Fifth Stage:
  Column: TSKGEL® ODS-80TM (4.6×150 mm, Toso)
  Eluent: 27% acetonitrile, 5% isopropyl alcohol, 0.1% TFA
  Mode: Isocratic elution
  Retention Time of OXM: 20.0 minutes As a result of the purification mentioned above, obtained was about 7 µg of OXM that gave a single peak on its chromatographic pattern.

The physicochemical properties of OXM are mentioned below, which were measured using the apparatus mentioned below.

Mass spectrograph: Nippon Electronics' JMS-HX110A (measured by the FAB method)

For amino acid analysis of OXM, employed was the method of B. A. Bidlingmeyer et al. (J. Chromatogr., 336, 93, 1984). Hydrolysis was carried out in hydrochloric acid vapor at 110° C. for 20 hours. The amino acid composition of the resulting hydrolysate was analyzed with PICO-TAG® amino acid analyzer (Waters).

Mass spectrometry: 4208±1 (M+H) measured
Amino acid analysis: measured (theoretical)
  Asx 3.5 (4), Glx 3.7 (4), Ser 4.3 (4), Gly 3.4 (3), His 1.1 (1), Arg 3.0 (3), Thr 4.5 (4), Ala 1.2 (1), Pro 1.2 (1) Tyr 2.1 (2), Val 0.9 (1), Met 0.8 (1), Leu 2.0 (2), Phe 2.0 (2), Lys 1.8 (2)
  (Trp is not analyzed; Asx is Asp or Asn; Glx is Glu or Gln.)

The primary structure of the amino acid sequence of OXM was determined through automatic Edman degradation of OXM (using PPSQ-10 Protein Sequencer, produced by Shimadzu) as combined with FAB-MS spectrometry, and through automatic Edman degradation of partial peptides (these were obtained as a result of digestion of OXM with lysylendopeptidase in 0.1M Tris-HCl buffer (pH 9) at 37° C. for 6 hours followed by reversed-phase HPLC) as combined with FAB-MS spectrometry.

Example 2 Synthesis of OXM

Herein used was a Shimadzu's peptide synthesizer, PSSM8 along with Shimadzu's reagents and solvents. According to the Shimadzu's program for peptide synthesis, the synthesizer was run to synthesize the intended peptide. The condensation of the amino acids was effected under ordinary conditions according to the Fmoc method (N. Izumiya et al., Pepuchido Gousei no Kiso to Jikken, published by Maruzen, 1985).

Precisely, 50 mg of a carrier resin (of p-benzyloxybenzyl alcohol type) having 23 µmols of Fmoc-Thr-OH bonded thereto was put into the reactor of the automatic synthesizer, and processed as follows in accordance with the Shimadzu's synthesis program.

(a) The carrier resin was washed with DMF for 3 minutes, and the DMF wash was discharged.

(b) DMF with 30% piperidine was added thereto, the resulting mixture was stirred for 4 minutes, and the DMF wash was discharged. This was repeated once again.

(c) The carrier resin was washed with DMF for 1 minutes, and the DMF wash was discharged. This was repeated five times. Thus was obtained a Thr-bonded carrier resin from which Fmoc was removed.

(d) 644 μl of DMF containing 184 μmols (62.0 mg) of Fmoc-Pro-OH, 184 μmols of PyBOP, 184 μmols of HOBt and 276 μmols of NMM was stirred for 3 minutes, and then added to the resin, and the resulting mixture was further stirred for 30 minutes. After this, the wash was discharged.

(e) The carrier resin was washed with DMF for 1 minute. This was repeated five times in all. Thus was formed Fmoc-Pro-Thr on the carrier. This was subjected to the above-mentioned steps (a) to (c) for washing and deprotection. Next, this was subjected to the step (d) for condensation where Fmoc-Gly-OH was used. Next, this was subjected to the washing step (e) to synthesize Fmoc-Gly-Pro-Thr on the carrier resin. Afterwards, the steps (a) to (e) were repeated in that order to finally obtain a carrier resin having a protected peptide bonded thereto. In the step (d), used were Fmoc-Gly-OH, Fmoc-Ser(tBu)-OH, Fmoc-Arg(Pmc)-OH, Fmoc-Lys (Boc)-OH, Fmoc-Ser(tBu)-OH, Fmoc-Asn(Trt)-OH, Fmoc-Met-OH, Fmoc-Leu-OH, Fmoc-Trp-OH, Fmoc-Gln(Trt)-OH, Fmoc-Val-OH, Fmoc-Phe-OH, Fmoc-Asp(OtBu)-OH, Fmoc-Gln(Trt)-OH, Fmoc-Ala-OH, Fmoc-Arg(Pmc)-OH, Fmoc-Arg(Pmc)-OH, Fmoc-Thr(tBu)-OH, Fmoc-Glu(OtBu)-OH, Fmoc-Leu-OH, Fmoc-Tyr(tBu)-OH, Fmoc-Lys(Boc)-OH, Fmoc-Ser(tBu)-OH, Fmoc-Tyr(tBu)-OH, Fmoc-Asp(OtBu)-OH, Fmoc-Asn(Trt)-OH, Fmoc-Thr(tBu)-OH, Fmoc-Phe-OH, Fmoc-Thr(tBu)-OH, Fmoc-Gly-OH, Fmoc-Gln(Trt)-OH, Fmoc-Ser(tBu)-OH and Fmoc-His(Trt)-OH of 184 μmols each, in that order. The thus-obtained carrier resin was washed with methanol and butyl ether, and then dried under reduced pressure for 3 hours. To this was added 800 μl of a mixture of TFA/H$_2$O/thioanisole/ethanediol/ethylmethylsulfide/thiophenol (82.5/5/5/2.5/3/2), and left at room temperature for 6 hours, whereby the peptide was cleaved from the resin. Next, the resin was removed through filtration, and about 15 ml of ether was added to the resulting filtrate. The precipitate thus formed was taken out and lyophilized to obtain 88.9 mg of a crude product of the peptide. This crude product was purified through high-performance liquid chromatography using a reversed-phase column (column: Shiseido's CAPCELL PAK® C18 SG120 S-5 μm; 30×250 mm). The purified product was eluted according to linear concentration gradient method with 0.1% TFA and acetonitrile as combined with detection at 220 nm. The fractions that gave the main peaks were fractionated, and a part thereof were subjected to the above-mentioned amino acid sequencing and mass spectrometry to obtain the fraction containing OXM. This fraction was concentrated and lyophilized to obtain 25.9 mg of the entitled compound.

The synthetic peptide as obtained in the manner mentioned above was analyzed according to the reversed-phase high-performance chromatography under the 5-stage purification conditions mentioned hereinabove, along with OXM obtained in Example 1, which verified that the both was eluted at the same position.

Mass spectrometry: M+H=4208 (theoretical: 4208)

Amino acid analysis:

Asx 3.6 (4), Glx 4.0 (4), Ser 4.0 (4), Gly 3.4 (3), His 1.0 (1), Arg 3.0 (3), Thr 4.0 (4), Ala 1.1 (1), Pro 1.0 (1) Tyr 2.0 (2), Val 1.0 (1), Met 0.9 (1), Leu 2.1 (2), Phe 2.0 (2), Lys 2.0 (2)

(Trp: not analyzed; Asx is Asp or Asn; Glx is Glu or Gln.)

According to the present invention, there is provided a novel peptide or pharmaceutically acceptable salts thereof, which have a cardiotonic activity and an insulin release-promoting activity and are useful for prevention or treatment of cardiopathy or diabetes.

What is claimed is:

1. A peptide according to (SEO ID NO: 1) or a pharmaceutically acceptable salt thereof.

2. A pharmaceutical composition comprising the peptide according to (SEO ID NO: 1) or a pharmaceutically acceptable salt thereof, and a pharmaceutically acceptable carrier.

3. A method for treating diabetes comprising administering the composition according to claim 2 to a patient in need thereof.

* * * * *

UNITED STATES PATENT AND TRADEMARK OFFICE
CERTIFICATE OF CORRECTION

PATENT NO. : 5,858,975

DATED : January 12, 1999

INVENTOR(S) : KEIICHI YANO, ET AL.

It is certified that error appears in the above-indentified patent and that said Letters Patent is hereby corrected as shown below:

On the title page, items

[54] TITLE

"RELEASE-BROMATING" should read --RELEASE PROMOTING--.

[56] REFERENCES CITED

PUBLICATIONS

After "Shinomura et al.,", "Regulatory Peptids," should read --Regulatory Peptides,--; and "Tanbi" should read -- Tani--.

COLUMN 1

Line 3, "RELEASE-BROMATING" should read --RELEASE-PROMOTING--;
Line 15, "BRIEF DESCRIPTION OF THE BACKGROUND" should read --2. Brief Description of the Background Art--;
Line 16, "ART" should be deleted;
Line 28, close up right margin;
Line 29, close up left margin;
Line 33, close up right margin; and
Line 34, close up left margin.

UNITED STATES PATENT AND TRADEMARK OFFICE
CERTIFICATE OF CORRECTION

PATENT NO. : 5,858,975
DATED : January 12, 1999
INVENTOR(S) : KEIICHI YANO, ET AL.

It is certified that error appears in the above-indentified patent and that said Letters Patent is hereby corrected as shown below:

COLUMN 3

```
Line 22, "and" should read --or--;
Line 53, "is" should read --are protected--;
Line 56, "are" should read --are protected--;
Line 58, "imidazolel" should read --imidazolyl--;
Line 59, "are" should read --are protected--;
Line 60, "is" should read --are protected--;
Line 66, "As the" should read --The--; and
Line 67, "(DMF), and" should read --(DMF);--.
```

COLUMN 5

Line 28, "salts" should read --salt--,

COLUMN 6

Line 61, "Precisely," should read --Precisely--.

COLUMN 7

Line 5, "minutes," should read --minute--.

UNITED STATES PATENT AND TRADEMARK OFFICE
CERTIFICATE OF CORRECTION

PATENT NO. : 5,858,975
DATED : January 12, 1999
INVENTOR(S) : KEIICHI YANO, ET AL.

It is certified that error appears in the above-indentified patent and that said Letters Patent is hereby corrected as shown below:

COLUMN 8

Line 17, "were" should read --was--;
    Line 26, "the" should be deleted;
    Line 27, "was" should read --were--.

Signed and Sealed this

Twenty-third Day of November, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
His  Ser  Gln  Gly  Thr  Phe  Thr  Asn  Asp  Tyr  Ser  Lys  Tyr  Leu  Glu  Thr
1                   5                        10                       15

Arg  Arg  Ala  Gln  Asp  Phe  Val  Gln  Trp  Leu  Met  Asn  Ser  Lys  Arg  Ser
               20                       25                       30

Gly  Gly  Pro  Thr
              35
```